United States Patent [19]

Klein et al.

[11] Patent Number: 5,279,565
[45] Date of Patent: Jan. 18, 1994

[54] INTRAVASCULAR TREATMENT APPARATUS AND METHOD

[75] Inventors: Enrique J. Klein, Los Altos; Aaron V. Kaplan, Palo Alto, both of Calif.

[73] Assignee: LocalMed, Inc., Sunnyvale, Calif.

[21] Appl. No.: 12,704

[22] Filed: Feb. 3, 1993

[51] Int. Cl.$^5$ .................. A61M 29/00; A61M 31/00
[52] U.S. Cl. .................................. 604/105; 604/53; 606/198
[58] Field of Search ............... 604/104–109; 49, 52, 53, 19, 22, 27, 28, 606/191, 194, 198

[56] References Cited

U.S. PATENT DOCUMENTS

| | | | |
|---|---|---|---|
| 597,988 | 1/1898 | Kroning et al. | 604/108 |
| 832,201 | 10/1906 | Kistler | 604/108 |
| 4,577,631 | 3/1986 | Kreamer | 606/198 |
| 4,585,000 | 4/1986 | Hershenson | 604/108 |
| 4,610,662 | 9/1986 | Weikl et al. | 604/53 |
| 4,636,195 | 1/1987 | Wolinsky | 604/53 |
| 4,660,571 | 4/1987 | Hess et al. | 604/105 |
| 4,824,436 | 4/1989 | Wolinsky | 604/53 |
| 5,011,472 | 4/1991 | Aebischer et al. | 604/53 |
| 5,030,201 | 7/1991 | Palestrant | 604/53 |
| 5,034,001 | 7/1991 | Garrison et al. | 604/53 |
| 5,087,244 | 2/1992 | Wolinsky et al. | 604/53 |

FOREIGN PATENT DOCUMENTS 1283614 8/1972 United Kingdom .............. 606/198

Primary Examiner—John D. Yasko
Assistant Examiner—Frank Wilkens, III
Attorney, Agent, or Firm—Townsend and Townsend Khourie and Crew

[57] ABSTRACT

An intravascular treatment apparatus provides means for infusing a treatment site with an agent and means for positioning the delivery interface against the treatment site which operate independently of one another. In a preferred embodiment, the apparatus includes a flexible body having a deflectable support frame at its distal end. A plurality of platforms, each comprising a plenum and a delivery interface, is coupled to the support frame. The platforms may be deployed radially from the body by deflecting the support frame using an actuator shaft extending through a passage in the body. The platforms are connected to a supply passage through the body. In this way, the apparatus may be positioned within a body lumen, usually an artery, with the platforms near a treatment site. By actuating the actuator shaft, the platforms are deployed against the treatment site. Independently of the platform deployment, a therapeutic agent may be supplied to the platforms and expelled through the delivery interface and into the treatment site to impregnate the treatment site.

72 Claims, 7 Drawing Sheets

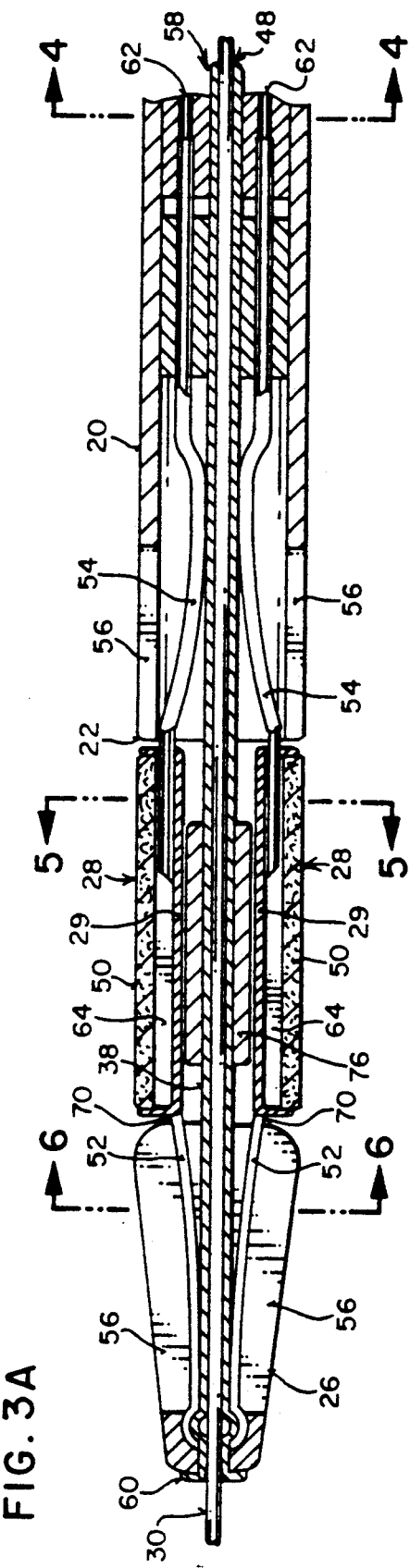

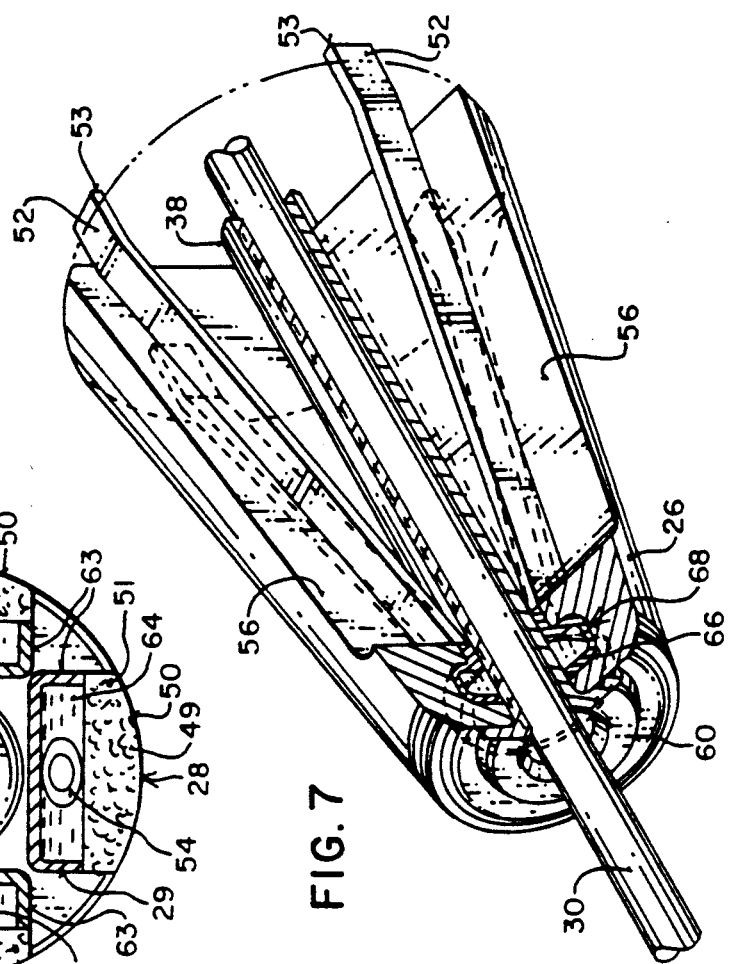
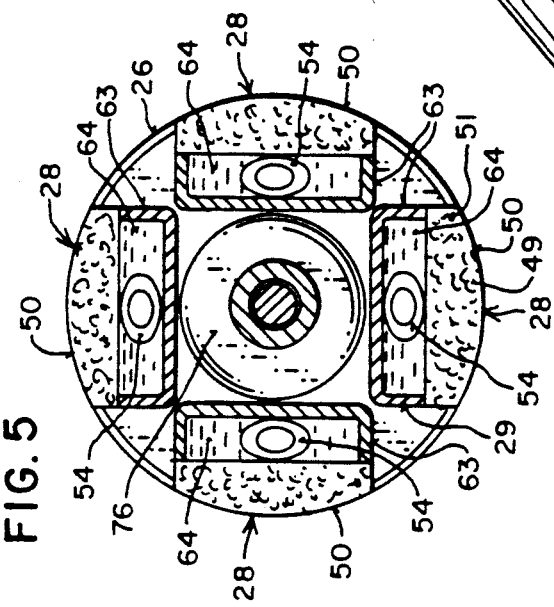
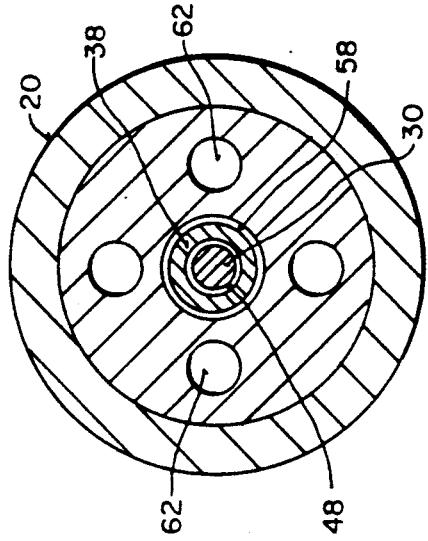
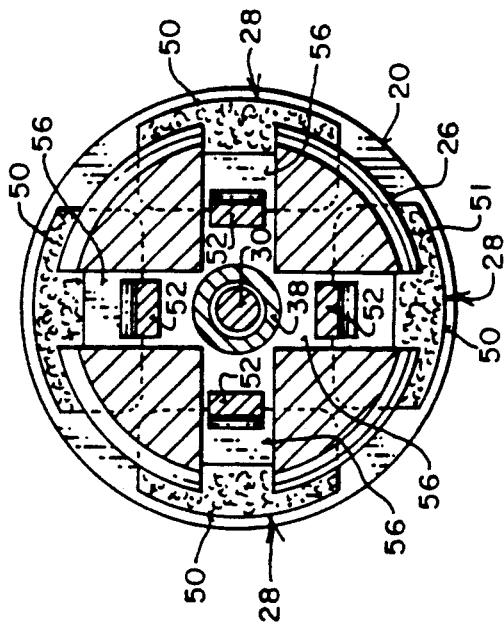

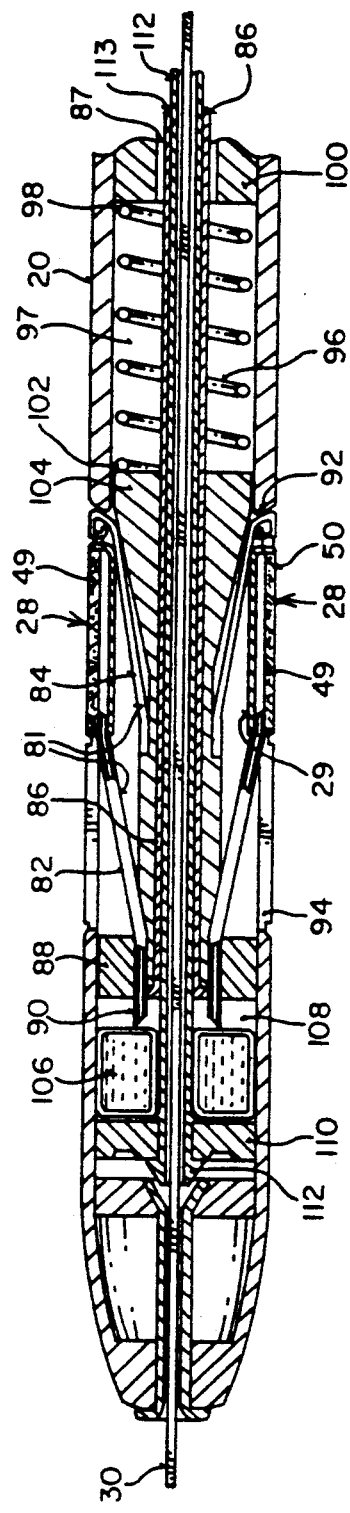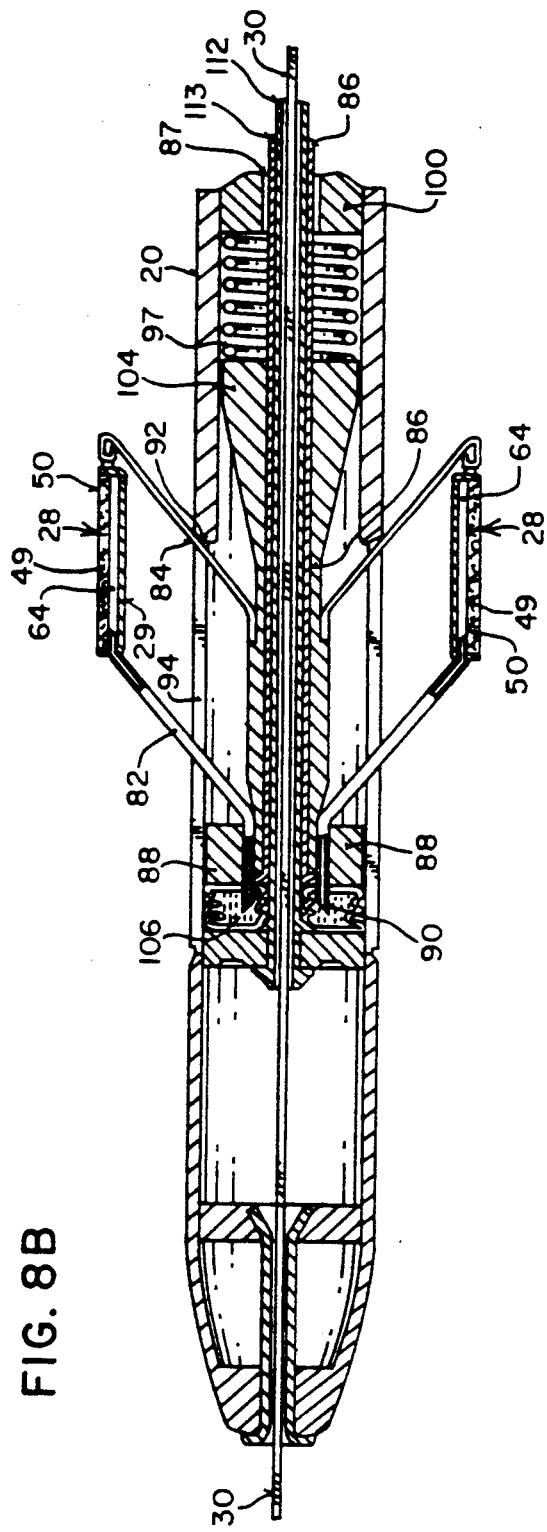

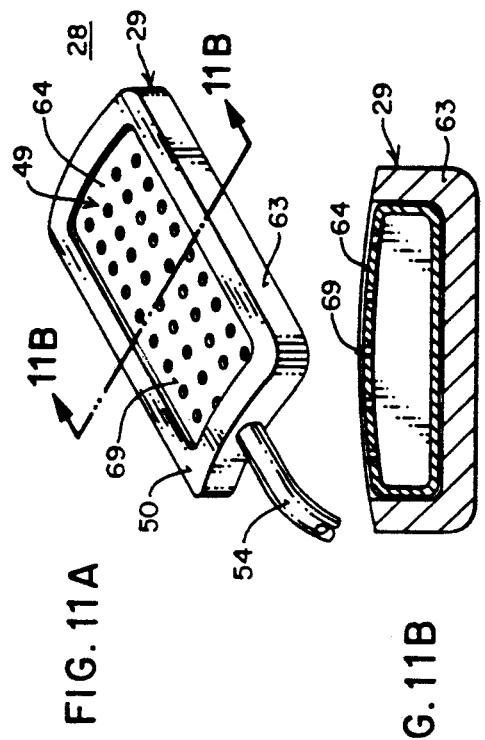
FIG. 11A
FIG. 11B
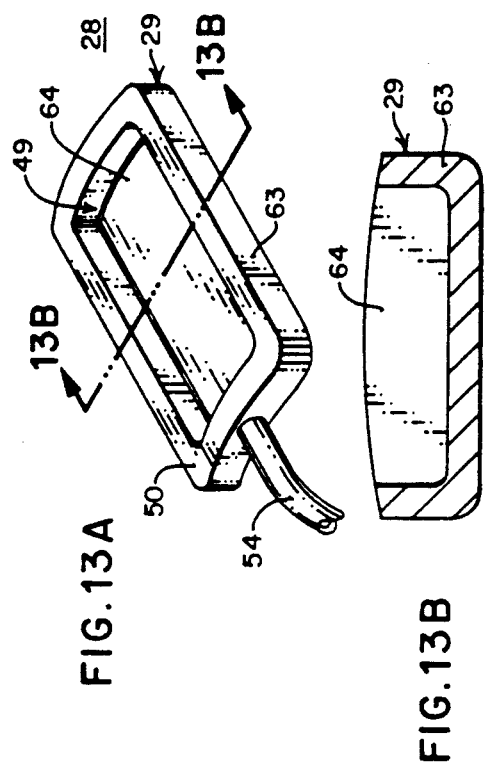
FIG. 13A
FIG. 13B
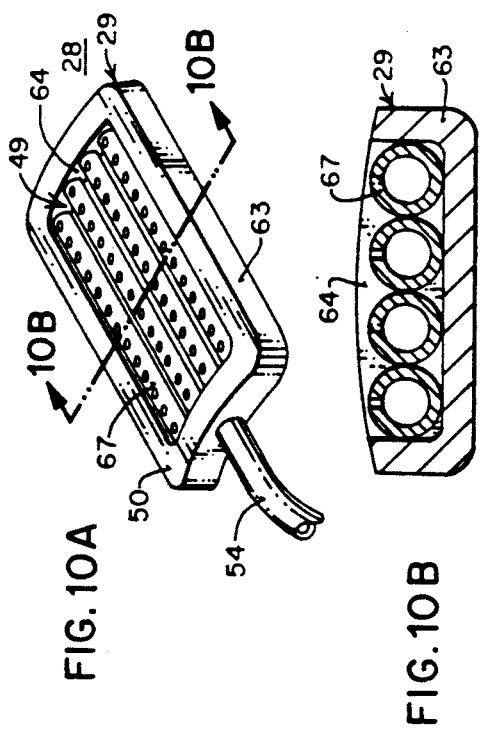
FIG. 10A
FIG. 10B
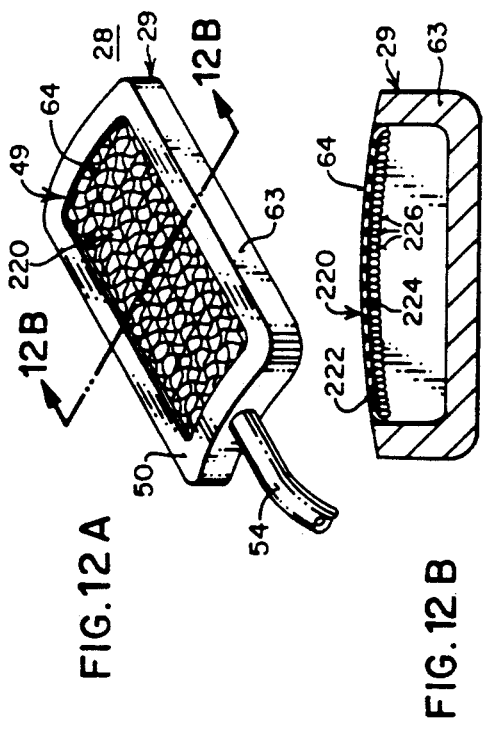
FIG. 12A
FIG. 12B

INTRAVASCULAR TREATMENT APPARATUS AND METHOD

BACKGROUND OF THE INVENTION

This invention relates generally to drug delivery devices, and more specifically to intravascular catheters for delivery of therapeutic agents from within a lumen of a blood vessel or other body organ.

In percutaneous transluminal angioplasty procedures, a catheter having a dilatation device such as a balloon at its distal end, is positioned in a lumen of a blood vessel with the dilatation device disposed within a stenotic region of the vessel. The dilatation device is then expanded in order to dilatate the vessel and restore adequate blood flow through the region of stenosis.

While angioplasty treatment frequently produces favorable results, it is not without problems. Primary among these are abrupt closure and restenosis. Abrupt closure refers to the acute interruption of blood flow at the site of angioplasty which typically occurs within the initial hours following the procedure. If arterial patency is not restored, acute myocardial infarction and death may occur. The primary mechanisms of abrupt closure are arterial dissection and/or thrombosis. The ability to maintain arterial dissections from occluding the vessel lumen via a deployable mechanism would allow perfusion of distal myocardium and reduce the complications associated with abrupt closure. Furthermore, it is postulated that the ability to deliver agent directly into the arterial wall (e.g. antithrombotic agents) would reduce thrombus formation and hence the incidence of abrupt thrombotic closure.

Restenosis refers to the re-narrowing of a vessel after an initially successful angioplasty procedure. Restenosis usually occurs within the first six months following angioplasty and is due to proliferation and migration of the cellular components of the vessel wall. Local delivery of agent would provide the means to achieve agent tissue concentrations far exceeding what is possible via systemic delivery. It is also postulated that the delivery of agent(s) directly into the arterial wall would interrupt the cellular proliferation and recruitment and hence reduce the incidence restenosis. Other interventional therapies used in the treatment of atherosclerosis, such as atherectomy, in which the stenotic region of the vessel is mechanically debulked to restore adequate blood flow through the stenotic region of the vessel, may equally benefit from such local delivery of agent (s).

The potential utility of local intramural drug delivery is not limited to atherosclerotic coronary artery disease. Other sites of atherosclerosis (e.g. renal, iliac, femoral, distal leg and carotid arteries as well as saphenous vein grafts, synthetic grafts and arterio-venous shunts used for hemodialysis) would also be appropriate vessels for local intramural drug delivery. Local intramural therapy using agent(s) may prove efficacious in non-arterial structures, including the prostrate via the prostatic urethra (benign prostatic hypertrophy, prostatitis and adenocarcinoma), fallopian tubes via its lumen (strictures), and brain parenchyma (Parkinson's Disease).

At present, intravenous medications are delivered systemically by vein, or regionally (e.g. intracoronary infusion). Systemic delivery is not well suited to the treatment of disease entities with a single site of interest (e.g., coronary artery disease) in that is necessitates: 1) exposing sites other than the site of interest to medication where is may have an adverse reaction; 2) sufficiently large quantities of agent within the entire volume of distribution to obtain the desired effect; and 3) exposing the agent to degradation and elimination by an organ system(s) remote from the site of interest. Furthermore, the agent tissue concentration within the site of interest is often limited by the detrimental effects of the agent at distant sites. Local intramural agent delivery obviates these problems. Therefore, it is of particular importance to deliver the therapeutic agent directly to the treatment site by intimate contact with or penetration into the tissue over a substantial portion of the luminal surface, rather than simply releasing the agent into the bloodstream in the vicinity of the treatment site.

While various catheters have been developed for local delivery of drugs to a treatment site within a vessel or organ lumen, such devices have suffered from certain drawbacks. In particular, known treatment apparatus do not permit the delivery of a drug directly to a treatment site independently of the deployment of the delivery interface against the lumen wall. For example, known treatment apparatus frequently employ an expandable member such as a balloon which is expanded at or near the treatment site and brought into contact with the lumen wall. A drug is infused through pores disposed either directly in the wall of the balloon, or in a second expandable member surrounding the balloon. In the former design, the drug itself serves as the expansion fluid for the balloon, with the drug being expelled through the porous surface of the expanded balloon. In the latter case, the drug is first delivered into the outer expandable member, and the balloon is then expanded so as to force the drug through the porous surface in the outer member. In both of these types of drug delivery devices, the drug cannot be infused without expanding the balloon, nor can the timing of drug infusion be controlled independently of balloon expansion.

Moreover, because such devices rely on a balloon-type expansion member to provide deployment of the porous infusion surface against the vessel wall, they completely occlude the vessel in the region of treatment when in their deployed configuration. This severely restricts, or even blocks entirely, blood flow through the vessel during treatment, preventing perfusion of tissue downstream from the treatment site. Therefore, the time such devices may be allowed to remain deployed is very limited, commonly for as little as one to two minutes. Catheters have been developed which have perfusion passages through the catheter shaft to allow blood to bypass through the device and perfuse the tissue downstream. However, due to size limitations and other design constraints, it is difficult to design such perfusion passages with sufficient blood flow capacity to allow deployment of the delivery device for relatively long periods of time. Furthermore, conventional perfusion balloon catheters, while able to maintain the blood vessel patent following a dilatation procedure, suffer from certain drawbacks, including the "flagging" of their amorphous structure when deflated, and the relatively limited vessel size range that a single device can be designed for. No such devices also able to do drug delivery are known to exist. In non-perfusing devices which employ the therapeutic agent itself as the expansion fluid for the balloon, the reversal of fluid flow required to deflate the balloon tends to draw blood into the device, preventing further use of the device until the blood has been expelled and the device has been refilled with agent. Typically, this prevents multiple treatments within the same vessel without withdrawing the catheter for purging or replacement.

It has also been recognized that alternative mechanisms to the existing devices utilizing balloon deployment to infuse an agent are unavailable in known treatment apparatus.

Another field of concern to the present invention is that of cellular seeding for repair of injured arterial tissue following angioplasty or atherectomy treatment. In the past decade there have been great advances in the technology enabling the culturing and transfecting of endothelial cells. Nable et al., have reported the ability to seed autologous endothelial cells transfected with the $\beta$-galactosidase gene upon injured arterial surface (Science 1989;xx:1343-44, incorporated herein by reference). Other investigators are working along similar lines. Most investigators have used a catheter system which isolates a site in the vessel by occluding the artery with balloons proximally and distally to that site. Cells are then introduced into the isolated portion. The efficacy of cell transfer by this approach is poor.

An intravascular treatment apparatus is therefore desired which can be used to administer therapeutic agents to a treatment site within the lumen of a blood vessel or other organ by direct contact with a substantial portion of the interior wall thereof. Desirably, the treatment apparatus will be deployable against the treatment site independently of the delivery of the agent to the site. Preferably, the deployment mechanism, when deployed, will maintain the vessel patent and allow substantial flow of blood to pass around it and perfuse the tissue distal to the treatment site for extended periods of time. Most desirably, the deployment mechanism will be a substantially rigid mechanical apparatus deployable and retractable by positive actuation from the proximal end of the apparatus. In addition, the apparatus should have a mechanism for delivering an agent to the treatment site which engages the treatment site along a porous contact surface and which is capable of injecting the agent at pressures sufficient to deeply penetrate tissue. The apparatus will preferably facilitate delivery of a variety of agent types and formulations, including pharmacological agents as well as endothelial cells for seeding purposes. Finally, the apparatus should be useful for treatment of blood vessels as well as a variety of other body organs.

DESCRIPTION OF THE BACKGROUND ART

Balloon-tipped catheters appropriate for angioplasty treatment procedures are described in, for example, U.S. Pat. Nos. 4,323,071, 4,292,974, 4,762,129, and 4,775,371. A catheter for locally applying medication to the wall of a blood vessel or other lumen is described in U.S. Pat. No. 5,087,244, the catheter having a balloon near its distal end which is expanded with a medication, which then flows through minute holes in the balloon surface at a low flow rate. U.S. Pat. No. 4,994,033 describes an intravascular treatment apparatus having a pair of expansion members concentrically arranged near its distal end wherein a drug is delivered to the outer expansion member, after which the inner expansion member is expanded, thereby expanding the outer member against the vessel wall and forcing the drug through minute holes in the outer member to bathe the vessel wall. U.S. Pat. No. 5,021,044 describes an intravascular treatment apparatus having a plurality of holes on the outer surface of the catheter body through which a drug may be delivered to a site within a vessel. U.S. Pat. No. 5,112,305 describes a catheter for delivery of therapeutic agents to an interior wall of a vessel, the catheter having a balloon near its distal end with tubular extensions projecting from its outer surface. A drug is delivered to the balloon which expands the balloon and flows through the tubular extensions into the vessel wall. Other drug delivery devices are described in U.S. Pat. Nos. 4,406,656, 5,015,232, 5,087,247, and 4,850,969.

SUMMARY OF THE INVENTION

The present invention provides an intravascular treatment apparatus for administering a therapeutic agent into a treatment site in the wall of a body lumen, while maintaining the vessel patent and permitting the flow of blood through the deployed mechanism so as to perfuse tissue distal to the treatment site. The treatment apparatus will have particular usefulness in treating arterial stenoses in connection with an angioplasty treatment, but will have further application in treating a variety of body organs, such as the prostate, the urogenital or the biliary ducts. The treatment apparatus is particularly advantageous over known devices because it permits deployment of the delivery mechanism against the treatment site independently of the delivery of the agent to the treatment site. The invention thereby provides means to mechanically maintain open arteries at the site of dissection to restore blood flow. The treatment apparatus has the further advantage of employing a resilient mechanical support frame rather than an inflatable expansion member for deploying the agent delivery mechanism against the treatment site, resulting in greater rigidity and improved deployment actuation capable of adjusting to a wide range of luminal diameters. The means of agent delivery is further improved over prior devices through the use of a substantially rigid platform with a porous surface which contacts the treatment site and infuses an agent at a pressure sufficient to achieve penetration over a substantial portion of the luminal surface.

In a preferred embodiment, the treatment apparatus of the present invention comprises a catheter body having a distal end, a proximal end and a passage therebetween; a support frame coupled to the catheter body incorporating a platform with delivery means, the support frame being movable between a retracted position adjacent the catheter body and a deployed position radially extended from the catheter body; an actuator shaft extending through the passage and coupled to the support frame for moving the support frame between the retracted and deployed positions; and independent means coupled to the support frame for delivering an agent to the treatment site through the platform, the delivery means being in contact with the treatment site in the deployed position.

The support frame may have a variety of configurations. In a specific embodiment, the support frame will comprise a first beam having a first end connected to the catheter body and a second end connected to the platform including the delivery means, the second end being radially deflectable from the catheter body. The support frame may be deployed by deflecting the second end of the beam. In one embodiment, a second beam is provided which has a third end connected to the actuator shaft and a radially deflectable fourth end connected to the platform, the distance between the first and third ends being greater than the distance between the second and fourth ends so as to form a generally trapezoidal shape. By pulling the actuator shaft, the third end of the second beam is drawn toward the first end of the first beam, thereby deflecting the second and fourth ends of the beams radially so as to deploy the platform against the treatment site. In an alternative embodiment, a cam means is mounted to the distal end of the actuator shaft which engages the first beam, so that moving the cam means relative to the first beam using the actuator shaft will radially deflect the second end so as to deploy the platform. In this embodiment, a second beam will usually connect the platform including the delivery means to the catheter body to form a parallelogram type linkage.

In a further embodiment, a first beam will connect to the platform including the delivery means to the actuator shaft, and cam means will be fixed to the catheter body near its distal end, whereby the beam is deflected radially when using the actuator shaft to engage the beam with the cam means. In this embodiment, a second beam will usually be connected between the platform including the delivery means and the actuator shaft, again forming a parallelogram type linkage.

The delivery means will comprise, in an exemplary embodiment, a rigid platform having a radially-facing contact surface and delivery interface for delivering the agent. The delivery interface may comprise, in various embodiments, a porous rigid matrix, such as sintered metal, a manifold of tubes with radially-facing perforations, or a bladder having a plurality of perforations on its radially-facing surface. Alternatively, the delivery interface may comprise a detachable porous membrane for applying a cell graft to the treatment site.

Usually, the agent is supplied from the proximal end of the catheter and communicated to the delivery means through one or more delivery passages in the catheter body, the delivery means being connected to the delivery passages by feeder tubes. Preferably, the feeder tubes are used as beams in the support frame, thereby performing dual tasks of communicating the agent to the delivery means as well as forming part of the support frame and deployment mechanism.

In an alternative embodiment, the agent may be contained in a capsule retained at the distal end of the catheter body. In this embodiment, a feeder tube extends between the capsule and the delivery means. A piston slidably disposed in the catheter body adjacent the capsule may be actuated from the proximal end of the catheter by a delivery actuator extending through the catheter body, whereby the piston compresses the capsule so as to force the agent contained therein through the feeder tubes to the platform including the delivery means.

In the method of the present invention, a treatment apparatus is transluminally positioned in a vessel with a distal end of the treatment apparatus adjacent the treatment site. A support frame at the distal end of the treatment apparatus is deployed and thus radially deflected so that a contact surface of a platform including delivery means coupled to the support frame is in intimal contact with the treatment site. An agent is supplied to the delivery means, and the agent is delivered to the treatment site through a delivery interface on the delivery means.

If desired, without deploying the support frame, an agent may be supplied through the delivery means to medicate the blood stream at and distal to the treatment site. After this, and by deploying the delivery means, an agent may be expelled through the delivery means to impregnate the treatment site. Usually, this is performed by supplying the agent through a delivery passage from the proximal end of the catheter. Alternatively, a piston may be actuated using an actuator extending to the proximal end of the catheter, the piston compressing a capsule containing the agent at the distal end, the capsule being connected to the delivery means. The agent may be administered to the luminal wall in a continuously pressurized stream, or alternatively in a pulsating pressurized stream to optimize the tissue impregnation process. Doses may be adjusted within very precise limits by using suitable pressurized dispensing means at the proximal end of the treatment apparatus. Advantageously, the method may further include discontinuing delivery of the agent, retracting the support frame with the delivery means, repositioning the treatment apparatus, and repeating the procedure at the same or a different treatment site without withdrawing the device from the vessel lumen.

Through the use of an expandable support frame rather than an inflatable balloon, the apparatus allows blood flow to continue to perfuse tissue downstream from the treatment site during treatment. In the deployed configuration of the support frame, blood may flood around the members of the support frame between the platforms and the catheter body. This permits treatments of long duration, as long as 20 minutes or more.

Further, by providing deployment of the delivery means independently of the delivery itself, the treatment apparatus of the present invention overcomes the prior art interdependence of deployment and delivery. The mechanical deploying means of the present invention provides rigidity during deployment as well as controlled retraction. The platforms of the delivery means provide increased rigidity and improved contact with the treatment site, for improved impregnation of a substantial portion of the luminal surface. Moreover, the use of the mechanically actuated support frame and rigid platform in place of the porous balloons of known devices permits the delivery means to be retracted from the vessel wall without the tendency to draw blood or other fluids into the treatment apparatus, thereby facilitating multiple treatments in the vessel without withdrawing the treatment apparatus from the patient and without risk of infusing diluted or contaminated fluids, but only the agent itself.

A further understanding of the nature and advantages of the invention may be realized by reference to the remaining portions of the specification and the drawings.

BRIEF DESCRIPTION OF THE DRAWINGS

FIG. 3A is a side cross-sectional view of a distal portion of the treatment apparatus of FIG. 1A with the delivery means in a retracted position.

FIG. 3B is a side cross-sectional view of a distal portion of the treatment apparatus of FIG. 1A with the delivery means in a deployed position.

FIGS. 4-6 are transverse cross-sectional views of the treatment apparatus of FIG. 3A at lines 4—4, 5—5 and 6—6, respectively.

FIG. 7 is a perspective view of a distal end of the treatment apparatus of FIG. 1A.

FIGS. 8A and 8B are side cross-sectional views of an alternative embodiment of a treatment apparatus constructed in accordance with the principles of the present invention.

FIGS. 10A and 10B are perspective and transverse cross-sectional views, respectively, of an exemplary embodiment of the delivery means of a treatment apparatus constructed in accordance with the principles of the present invention.

FIGS. 11A and 11B are perspective and transverse cross-sectional views, respectively, of a further embodiment of the delivery means of the treatment apparatus of the present invention.

FIGS. 12A and 12B are perspective and transverse cross-sectional views, respectively, of another embodiment of the delivery means of the treatment apparatus of the present invention.

FIGS. 13A and 13B are perspective and transverse cross-sectional views, respectively, of still another embodiment of the delivery means of the treatment apparatus of the present invention.

DESCRIPTION OF SPECIFIC EMBODIMENTS

Figure 1A:
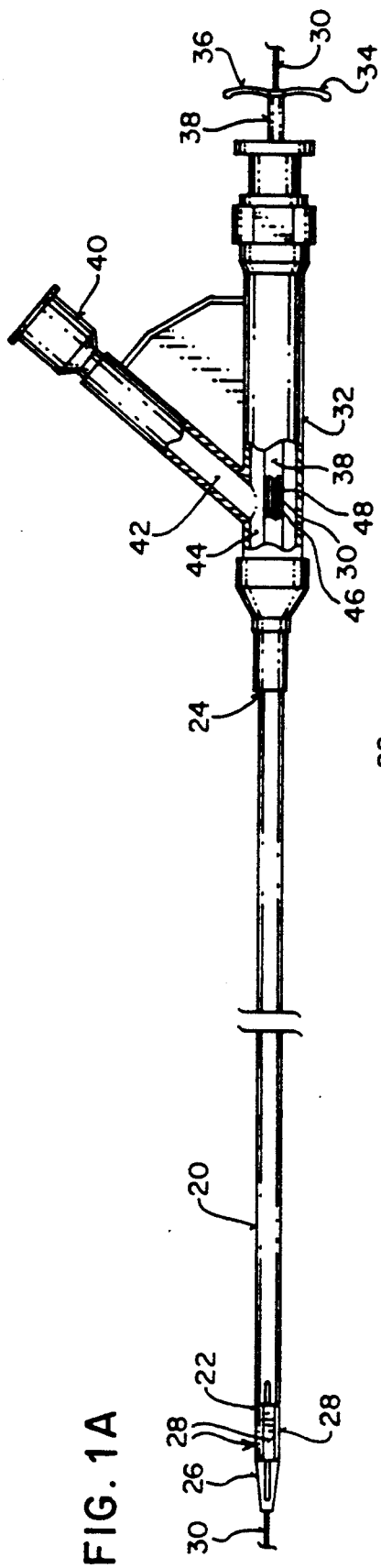
FIG. 1A is a side elevational view of a treatment apparatus constructed in accordance with the principles of the present invention.

Referring to FIG. 1A, the intravascular treatment apparatus of the present invention includes an elongate flexible catheter body 20 having a distal end 22 and a proximal end 24. A nose cone 26 is disposed distally of distal end 22 and is movable in the axial direction relative to body 20. Delivery means 28 is coupled to nose cone 26 and body 20, as described in detail below. A movable guidewire 30 extends through the treatment apparatus and beyond its distal end 22.

A proximal housing 32 is attached to proximal end 24 of catheter body 20. Proximal housing 32 includes a deployment actuator 34 having a pair of finger grips 36 attached to an actuator shaft 38 which extends through body 20 to nose cone 26. An agent supply port 40 extends laterally from housing 32, to which may be connected a syringe or other device for supplying a therapeutic agent to the treatment apparatus. Supply port 40 has a supply lumen 42 communicating with an annular plenum or manifold 44 in housing 32. The interior of housing 32 includes, in addition to annular plenum 44, a central passage 46 within which actuator shaft 38 is slidably disposed. Actuator shaft 38 further includes a guidewire passage 48 through which guidewire 30 passes.

Figure 1B:
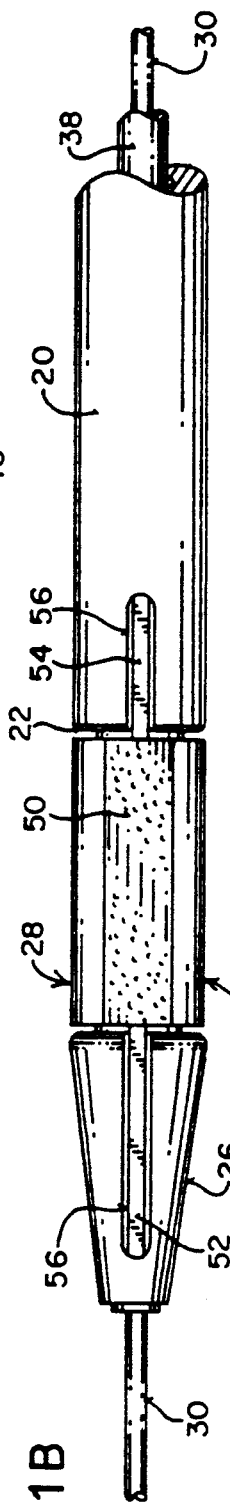
FIG. 1B is a side elevational view of a distal portion of the treatment apparatus of FIG. 1A.
Figure 2:
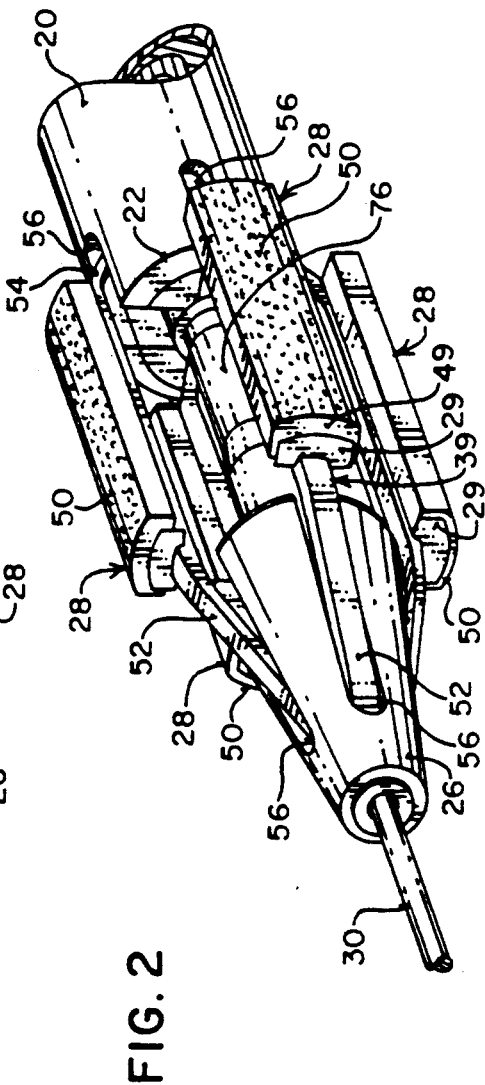
FIG. 2 is a perspective view of the distal portion of the treatment apparatus of FIG. 1A with the delivery means in a deployed position.

Referring now to FIGS. 1B and 2, the distal portion of the intravascular treatment apparatus will be described. Delivery means 28 comprises a plurality of rigid platforms 29, each coupled to catheter body 20 and nose cone 26 by means of a support frame 39. Support frame 39 comprises a distal beam 52 attached to nose cone 26 and a proximal beam 54 attached to catheter body 20, forming a linkage generally trapezoidal in shape. A delivery interface 49 is disposed on a radially-facing side of each platform 29.

Preferably, beams 52, 54 will have flexibility and resiliency so as to deflect radially outward when nose cone 26 is pulled toward catheter body 20, as described more fully below. Alternatively, beams 52, 54 may be substantially rigid and pivotally attached to nose cone 26 and catheter body 20 so as to pivot radially outward. Beams 52, 54 will, in any event, have sufficient rigidity to provide a radial expansion force against the vessel wall in tight contact between contact surfaces 50 and the treatment site.

In the retracted position, beams 52, 54 are nested within the perimeter of catheter body 20 and nose cone 26, with contact faces 50 generally being flush with the exterior surface of the treatment apparatus. Slots 56 are provided in nose cone 26 and the distal end 22 of catheter body 20, so that, when the platforms are deployed, beams 52, 54 can freely move radially outward.

As illustrated in FIGS. 3A-3B, actuator shaft 38 extends through a passage 58 in catheter body 20 and attaches to a distal end 60 of nose cone 26. Proximal beams 54, in a preferred embodiment, comprise feeder tubes which are connected at their proximal ends to agent delivery passages 62 in the catheter body 20. Agent delivery passages 62 are in communication with annular plenum 44 in proximal housing 32. Feeder tubes 54 are attached at their distal ends 55 to platforms 29, in communication with a plenum 64 in an interior portion of each platform.

Distal beams 52 connect platforms 29 to nose cone 26. As best seen in FIG. 7, distal beams 52 are connected, or made integral with, an annular ring 66 at their distal ends which is retained in a toroidal aperture 68 in the distal portion of nose cone 26. Beams 52 extend proximally from ring 66 within slots 56 of nose cone 26, and are configured to flare radially outward to their proximal ends 53 attached to platforms 29. Referring to FIG. 3B, it can be seen that proximal movement of nose cone 26 will cause the ends 53, 55 of flexible beams 52, 54 to deflect radially, thereby deploying platforms 29 while maintaining contact surfaces 50 in a substantially constant orientation relative to the catheter body 20 (and the vessel wall).

When deployment of platforms 29 is desired, finger grips 36 at the proximal end of the actuator shaft 38 are pulled proximally relative to catheter body 20, translating nose cone 26 in a proximal direction. Ends 53, 55 of beams 52, 54 deflect such that platforms 29 are deployed radially outward bringing contact surfaces 50 against the interior wall of the vessel. An agent may then be supplied through supply port 40, delivery passage 62 and feeder tubes 54 into plenum 64, whereupon the agent will be delivered through delivery interface 49 to impregnate the treatment site in the vessel wall.

FIG. 4 illustrates a cross-section of catheter body 20. Body 20 includes, in a preferred embodiment, a plurality of delivery passages 62, usually one delivery passage for each platform 29. Alternatively, a single delivery passage may be provided in body 20, with a manifold (not shown) at the distal end 22 by which the agent may be distributed to each feeder tube and platform. Body 20 further includes the central passage 58 within which the actuator shaft 38 is slidably disposed. As described above, actuator shaft 38 has a guidewire passage 48 through which a guidewire 30 may be inserted for guiding the treatment apparatus into its position within the vessel.

FIG. 5 illustrates a cross-section of a distal portion of the apparatus of the present invention. It can be seen that the four platforms 29 are arranged such that each contact surface 50 faces in an angular direction of approximately 90° to each adjacent platform. Preferably, the contact surfaces are rounded so as to provide a minimally circular introducing profile for the treatment apparatus while also presenting a conforming contact with the wall of the vessel. A lower portion of each platform 29 comprises a rigid non-porous base 63 with an interior aperture defining a plenum 64. Plenum 64 is sealed on its open radial side by delivery interface 49 which in this embodiment, comprises a porous matrix 51. A core member 76 is disposed about actuator shaft 38 against which bases 63 of platforms 29 rest in their retracted position.

In a preferred embodiment, porous matrices 51 are composed of sintered metal, such as stainless steel. The sintered structure provides a rigid surface for non-deforming contact with the treatment site while having the appropriate porosity to infuse a therapeutic agent therethrough. Preferably, the pores of matrices 51 will be configured to inject the agent into the treatment site at a pressure sufficient to attain deep impregnation into the adventitial layer of the vessel or wall tissue of another organ. Porous sintered metals of various porosity and fabricated in various geometries are available from, for example, Mott Metallurgical corporation, Farmington Industrial Park, Farmington, Conn. 06032. In a specific embodiment, porous matrices 51 will comprise sintered stainless steel plates having a filtration grade in the range of 0.2 to 100 microns, and preferably in the range of 10 to 50 microns.

FIG. 6 illustrates a cross-section of nose cone 26 of the embodiment of FIGS. 1-3. It can be seen that slots 56 in nose cone 26 form a cross shape, with each of distal beams 52 extending through a slot 56. In a retracted position, contact surfaces 50 of porous matrices 51 are substantially flush with the exterior surface of catheter body 20 and the proximal end of nose cone 26.

Alternative embodiments of delivery means 28 are shown in FIGS. 10-13. In each of these embodiments, delivery means 28 comprises a platform 29 having a rigid base 63 defining an aperture 64. Delivery interface 49 is disposed within aperture 64. A contact surface 50 sealed into aperture 64 provides contact with the vessel wall in the deployed position.

In the embodiment of FIGS. 10A and 10B, delivery interface 49 comprises a manifold of tubes 67 comprising a plurality of perforate tubes in communication with feeder tube 54. Manifold 67 may be plastic or metal material with radially facing orifices formed at selected locations along the tubes.

In FIGS. 11A-11B, delivery interface 49 comprises a perforate bladder 69, which may be flexible or rigid, disposed within aperture 64 in communication with feeder tube 54.

Referring to FIGS. 12A-12B, delivery interface 49 comprises an endothelial patch 220 fixed to base 63 so as to cover plenum 64. Endothelial patch 220 consists of a support membrane 222, comprising, for example, a permeable or semipermeable fabric such as Gortex ™. On an inward-facing surface 224 of membrane 222, endothelial cells 226 have been cultured. When platforms 29 have been deployed to be in close opposition to the arterial wall, an aqueous vehicle is communicated to plenum 64 under pressure, causing endothelial cells 226 to migrate through membrane 222, thereby providing endothelial cell seeding of the vessel wall.

In a further embodiment, illustrated in FIGS. 13A-13B, delivery interface 49 comprises simply an open plenum 64. In this embodiment, platforms 29 are deployed such that contact surfaces 50 seal against the vessel wall. A therapeutic agent, which may comprise a pharmacological agent or endothelial cells in a culture medium, is communicated to plenum 64 through feeder tubes 54. By maintaining platforms 29 against the vessel wall for an extended period of time, effective impregnation and/or cellular seeding of the treatment site is achieved.

Alternative embodiments of the apparatus of the present invention are illustrated in FIGS. 8 and 9. In the embodiment to FIGS. 8A and 8B, platforms 29 are radially deployable from body 20 by means of a parallelogram-type support frame 81. Support frame 81 includes a pair of beams 82, 84 linking platforms 29 to a distal end of actuator shaft 86. Proximal beam 84 is attached to a proximal end of platform 29, and on its opposite end to an extension 104 of actuator shaft 86. Distal beam 82 will preferably comprise a feeder tube extending into plenum 64 of platform 29 and fixed at its opposing end to a distal, radially enlarged portion 88 of extension 104 of actuator shaft 86. Distal ends 90 of feeder tubes 82 are cut at an angle to provide a sharp tip and extend distally of enlarged distal portion 88 of extension 104 of actuator shaft 86.

Actuator shaft 86 is slidably disposed in a passage 87 in body 20 and extends to the proximal end of the treatment apparatus, where the treatment apparatus shaft will have a handle or similar means for grasping by the user (not shown). It can be seen that by exerting a proximal force on actuator shaft 86, distal radially enlarged, portion 88 pulls with it beams 82, 84. A portion of distal end 92 of catheter body 20 provides a camming surface which forces proximal beam 84 radially outward, as shown in FIG. 8B. Beams 82, 84 have sufficient flexibility and resilience to flex radially outward, while having sufficient rigidity to maintain tight contact between contact surface 50 and the treatment site. Slots 94 formed in the distal end of catheter body 20 allow beams 82 and 84 to extend radially outward as actuator shaft 86 is pulled proximally.

In this embodiment, the treatment apparatus further includes a spring 96 disposed about actuator shaft 86 and residing within an aperture 97 within catheter body 20. The proximal end 98 of the spring engages block 100 fixed in catheter body 20, while distal end 102 of the spring is engaged by extension 104 on actuator shaft 86. Translation of actuator 86 further compresses spring 96. Release of actuator shaft 86 will allow spring 96 to return to its originally pre-loaded configuration, up to a proximal stop for actuator shaft 86 (not shown), providing an automatic retraction of platforms 29 by release of force on the proximal end of actuator shaft 86.

FIGS. 8A, 8B also illustrate a second preferred embodiment for communicating an agent to the delivery means 28. In this embodiment, agent-containing capsules 106 of toroidal configuration are retained in an aperture 108 distally of distal end 88 of enlarged portion 88 of extension 104 of actuator shaft 86. Capsules 106 comprise a collapsible material, such as plastic. A piston 110 is slidably disposed within aperture 108 distally of capsules 106. Piston 110 is attached to the distal end of agent delivery actuator shaft 112 which extends proximally to the proximal end of catheter body 20 within a passage 113 in actuator shaft 86. Initially, capsules 106 are disposed distally of the sharp ends 90 of feeder tubes 82. When delivery means 28 have been deployed against the treatment site and the agent is to be administered, delivery actuatory 112 is pulled in the proximal direction so that piston 110 pushes capsules 106 against feeder tube tips 90, thereby piercing capsules 106. Further movement of actuator 112 in the proximal direction collapses capsules 106, forcing the agent contained therein through feeder tubes 82 into plenum 64 of platforms 29 and through delivery interface 49 to impregnate the treatment site.

While the agent-containing capsules 106 are illustrated in conjunction with a parallelogram-type support frame in FIGS. 8A and 8B, it should be understood that such an agent delivery mechanism may also be used with the trapezoidal support frame embodiment described above in connection with FIGS. 1-7. Similarly, an agent may be delivered to the delivery means in the devices of FIGS. 8A and 8B through a delivery passage from a proximal end of the treatment apparatus as in FIGS. 1-7, rather than using capsules 106 at the distal end of the device.

Figure 9A:
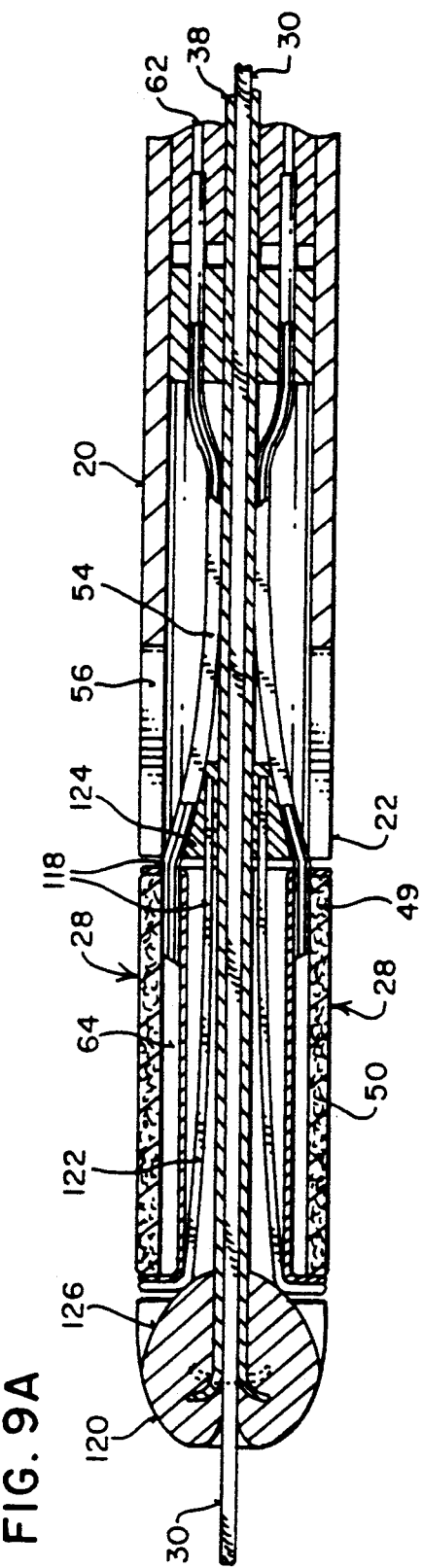
FIGS. 9A and 9B are side cross-sectional views of a further embodiment of a treatment apparatus constructed in accordance with the principles of the present invention.
Figure 9B:
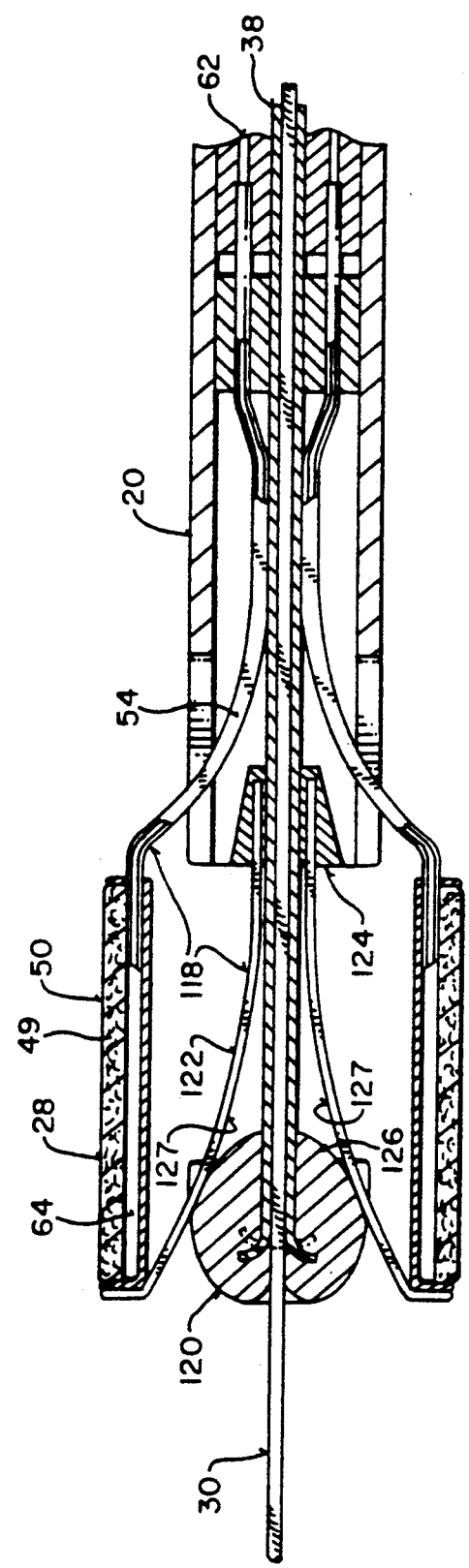

A further embodiment of the intravascular treatment apparatus of the present invention is shown in FIGS. 9A and 9B. In this embodiment, feeder tubes 54 serving as proximal beams of support frame 118 extend from agent delivery passages 62 to plenums 64 in platforms 29. Feeder tubes 54 can flex radially outward in slots 56 at the distal end of catheter body 20. In these respects, the embodiment of FIGS. 9A and 9B is similar to that described above in connection with FIGS. 1-7.

This embodiment differs, however, in that, rather than employing a trapezoidal deflectable support frame as shown in FIGS. 1-7, the apparatus includes a cam 120 distally of delivery means 28 which is attached to the distal end of actuator shaft 38. Distal beams 122 connect platforms 29 to a core member 124 which forms part of catheter body 20. Camming surfaces 126 are provided on a proximal side of cam 120 and engage the inner surfaces 127 of distal beams 122. By translating actuator shaft 38 and cam 120 in a proximal direction, distal beams 122 are forced radially outward, causing proximal beams 54 to flex and/or pivot radially outward, maintaining contact surfaces 50 in a substantially constant orientation relative to body 20. When platforms 29 have been deployed to the desired position, an agent may be delivered through delivery passage 62 and feeder tubes 54 into plenum 64, and through delivery interface 49 to impregnate the treatment site.

It should be understood that the apparatus of the present invention is suitable for delivery of a variety of therapeutic agents including low molecular weight, pharmaceuticals, proteins, peptides, nucleotides, carbohydrates, muccopolysaccharides, simple sugars and steroids. The present invention facilitates delivery of such agents in a variety of formulations, including aqueous vehicle or liposome. The apparatus is further useful for delivery of viral particles (to facilitate gene transfer) or for cellular seeding (e.g. endothelial, monocytic, or myocytic cells). The agents delivered may perform a variety of functions including anti-thrombotics, anti-metabolics, growth factor inhibitors, growth promoters, anticoagulants, antimitotics and antibiotics.

Figure 14A:
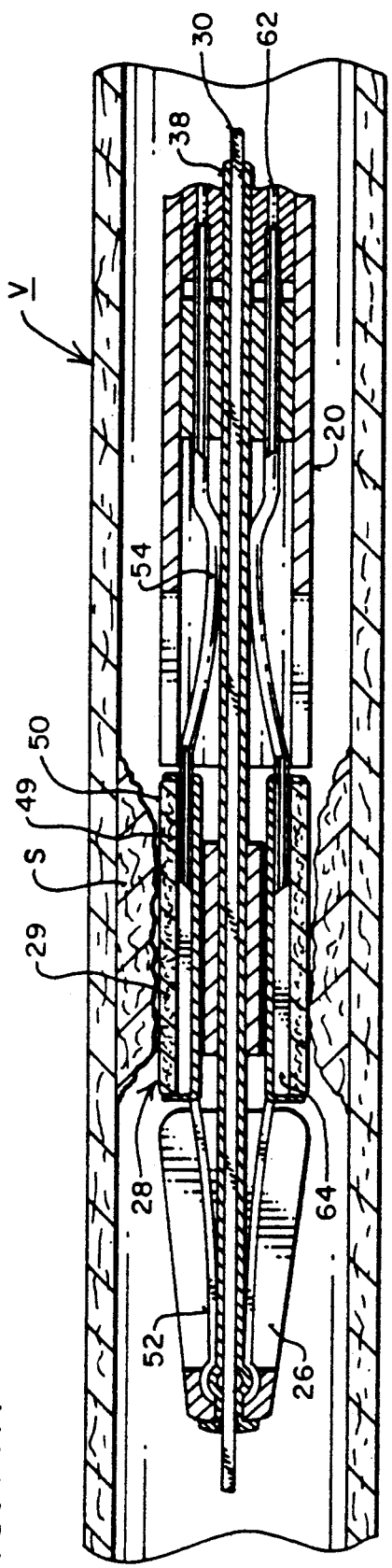
FIGS. 14A and 14B illustrate a distal portion of the treatment apparatus of FIG. 1 positioned in a stenotic region of a vessel according to the method of the present invention.
Figure 14B:
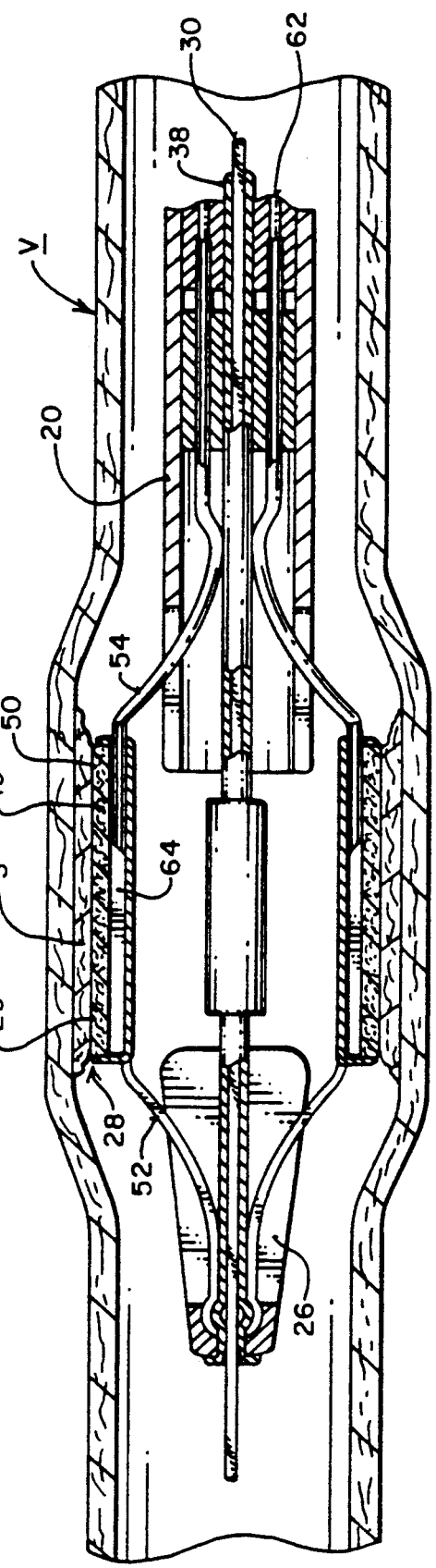

In a preferred embodiment of the method of the present invention, as shown in FIGS. 14A and 14B, the apparatus is positioned translumininally in a body lumen or vessel V which will typically be an artery. The apparatus will be positioned such that delivery means 28 is disposed near the treatment site, which will most often be a region of stenosis S in an artery. Usually, a movable guidewire 30 will be used to guide the treatment apparatus through the artery. A fixed guidewire attached to the distal end of the treatment apparatus may be used instead of or in conjunction with movable guidewire 30.

When the treatment apparatus has been positioned near the treatment site S, platforms 29 are radially deployed by pulling actuator shaft 38, causing beams 52, 54 to deflect radially outward. Preferably, platforms 29 are extended such that contact surfaces 50 engage the treatment site S in tight contact therewith.

When delivery of an agent is desired, the agent is supplied to the delivery means 28 either through an agent supply port 40 at the proximal end of the treatment apparatus and agent supply passages 62 (FIG. 1), or by actuating a delivery actuator to pierce agent-containing capsules 106 in the distal end of the device and collapse the capsules to expel the agent contained therein (FIGS. 8A and 8B). The agent will be communicated into plenums 64 of platforms 29, and infused through delivery interface 49 to impregnate the treatment site S. In a preferred embodiment, delivery interface 49 will be configured to inject the agent into the treatment site at varying pressures, with higher pressures being sufficient to attain deep impregnation into the adventitial layer of the vessel, or up to the outermost regions of another organ wall.

Once treatment at a particular site has been completed, delivery of the agent may be terminated, and, if desired, the platforms 28 retracted by distal movement of actuator shaft 38. Alternatively, further infusion of the agent may be performed at treatment site S. When treatment of the site is complete, the apparatus may be removed from the vessel, or repositioned within the same vessel without removing it, and the procedure repeated by re-deploying the platforms and impregnating a new treatment site with the agent.

Where cellular seeding is to be performed, the delivery means 28 will be deployed to engage the vessel wall, forming a seal between contact surfaces 50 of platforms 29 and the wall tissue. Delivery means 28 will preferably comprise one of the embodiments illustrated in FIGS. 12 and 13. Using the embodiment of FIGS. 12A and 12B, support membrane 220 is held against the treatment site, support membrane 220 being porous and having endothelial cells 226 cultured on its surface opposite that contacting the treatment site. An aqueous vehicle is then communicated to plenums 64 in platforms 29 under sufficient pressure to cause transfer of cells 226 across membrane 220 and into the vessel tissue, thereby effecting cellular seeding of the treatment site. Similarly, using the delivery interface 49 of FIGS. 13A and 13B, platforms 29 are deployed against the vessel wall to form a seal against contact surface 50. Endothelial cells in fluid suspension are then communicated to plenums 64, where they are maintained in close opposition to the treatment site for sufficient time to effect cellular seeding.

Using the apparatus and method of the present invention, treatment of a particular site in a vessel or organ lumen may be performed for extended periods without danger of tissue necrosis downstream from the treatment site. Because the mechanically-actuated support frame of the invention does not occupy the entirety of the lumen in the area of treatment as do inflatable balloon-type expansion devices, blood may flow around the treatment apparatus and between the delivery means and the catheter body, thereby perfusing downstream tissue during treatment. This facilitates treatments of up to 20 minutes or more, a period unobtainable using known devices. Such extended treatments are particularly advantageous in cellular seeding, where extended and continuous exposure of endothelial cells to the arterial surface results in significantly improved cell transfer and adhesion. Moreover, extended exposure of vessel tissue to a pharmacological agent will result in improved impregnation and therapeutic effect in the treatment site.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for administering a therapeutic agent to a treatment site in a body lumen, the apparatus comprising:
    a catheter body having a distal end, a proximal end and a passage therebetween;
    a support frame coupled to the catheter body, the support frame being movable between a retracted position adjacent the catheter body and a deployed position radially extended from the catheter body;
    an actuator shaft extending through the passage and having a distal end for engaging the support frame for moving the support frame between the retracted and deployed positions; and
    means coupled to the support frame for delivering the agent radially outwardly from the support frame under fluid pressure to the treatment site, the delivery means being in contact with the treatment site in the deployed position.

2. The apparatus of claim 1 wherein the support frame comprises at least a first beam having a first end connected to the catheter body and a second end connected to the delivery means, the second end being radially deflectable from the catheter body.

3. The apparatus of claim 2 wherein the support frame further comprises a second beam having a third end connected to the actuator shaft and a radially-deflectable fourth end connected to the delivery means, the distance between the first and third ends being greater than the distance between the second and fourth ends, wherein the third end may be drawn toward the first end by the actuator shaft to radially deflect the second and fourth ends.

4. The apparatus of claim 2 further comprising cam means attached to the distal end of the actuator shaft, the cam means movable against the first beam by means of the actuator shaft to deflect the second end.

5. The apparatus of claim 1 wherein the support frame comprises a first beam having a first end connected to the actuator shaft and a second end connected to the delivery means, wherein the second end is radially deflectable from the catheter body.

6. The apparatus of claim 5 further comprising cam means fixed to the catheter body near the distal end, the cam means configured to engage the first beam by moving the actuator shaft, thereby deflecting the second end.

7. The apparatus of claim 1 wherein the means for delivering the agent comprises a platform having a contact surface for contacting the treatment site in the deployed position, and a delivery interface through which the agent is delivered.

8. The apparatus of claim 7 wherein the delivery interface comprises a rigid porous matrix.

9. The apparatus of claim 8 wherein the porous matrix is sintered metal.

10. The apparatus of claim 7 wherein the delivery interface comprises a perforate bladder.

11. The apparatus of claim 7 wherein the delivery interface comprises a manifold of perforate tubes.

12. The apparatus of claim 7 wherein the delivery interface comprises an open plenum on the platform, the contact surface being disposed about the periphery of the plenum.

13. The apparatus of claim 7 wherein the delivery interface comprises a support membrane for applying a cell graft.

14. Apparatus for administering a therapeutic agent to a treatment site in a body lumen, the apparatus comprising:
    a catheter body having a distal end, a proximal end and a passage therebetween;
    a support frame coupled to the catheter body, the support frame being movable between a retracted position adjacent the catheter body and a deployed position radially extended from the catheter body;
    an actuator shaft extending through the passage and having a distal end for engaging the support frame for moving the support frame between the retracted and deployed positions;
    a platform coupled to the support frame, the platform having a contact surface for contacting the treatment site in the deployed position and a delivery interface for delivering the agent under fluid pressure to the treatment site.

15. The apparatus of claim 14 wherein the support frame comprises at least a first beam having a first end connected to the catheter body and a second end connected to the platform, the second end being radially deflectable from the catheter body.

16. The apparatus of claim 15 wherein the support frame further comprises a second beam having a third end connected to the actuator shaft and a radially-deflectable fourth end connected to the platform, the distance between the first and third ends being greater than the distance between the second and fourth ends, wherein the third end may be drawn toward the first end by the actuator shaft to radially deflect the second and fourth ends.

17. The apparatus of claim 15 further comprising cam means attached to the distal end of the actuator shaft, the cam means movable against the first beam by means of the actuator shaft to deflect the second end.

18. The apparatus of claim 14 wherein the support frame comprises a first beam having a first end connected to the actuator shaft and a second end connected to the delivery interface, wherein the second end is radially deflectable from the catheter body.

19. The apparatus of claim 18 further comprising cam means fixed to the catheter body near the distal end, the cam means configured to engage the first beam by moving the actuator shaft, thereby deflecting the second end.

20. The apparatus of claim 14 wherein the delivery interface comprises a rigid porous matrix.

21. The apparatus of claim 20 wherein the porous matrix is sintered metal.

22. The apparatus of claim 14 wherein the delivery interface comprises a perforate bladder.

23. The apparatus of claim 14 wherein the delivery interface comprises a manifold of perforate tubes.

24. The apparatus of claim 14 wherein the delivery interface comprises an open plenum on the platform, the contact surface being disposed about the periphery of the plenum.

25. The apparatus of claim 14 wherein the delivery interface comprises a support membrane for applying a cell graft.

26. The apparatus of claim 14 further comprising means for communicating the therapeutic agent to the delivery interface.

27. The apparatus of claim 26 wherein the communicating means comprises a delivery passage through the catheter body, a distal end of the delivery passage being connected to the delivery interface by a feeder tube.

28. The apparatus of claim 26 wherein the communicating means comprises a collapsible drug-containing capsule disposed in an aperture at the distal end of the catheter body, and a feeder tube for connecting the capsule to the delivery interface.

29. The apparatus of claim 28 further comprising a drug supply actuator for collapsing the capsule, the drug supply actuator comprising a piston slidably disposed in the aperture and a rod coupled to the piston and extending through an actuator passage in the catheter body.

30. The apparatus of claim 29 wherein the feeder tube is selectively connectable to the capsule.

31. The apparatus of claim 30 wherein the capsule is slidably disposed in the aperture so as to be movable into engagement with the feeder tube by the piston.

32. The apparatus of claim 31 wherein the feeder tube comprises a sharpened tip for piercing the capsule.

33. A method of administering a therapeutic agent to a treatment site in a wall of a vessel, the method comprising the steps of:
 translumially positioning a catheter in the vessel with a distal end of the catheter adjacent the treatment site;
 radially extending a support frame at the distal end of the catheter such that a contact surface of delivery means coupled to the support frame is against the treatment site;
 communicating the therapeutic agent to the delivery means; and
 delivering the therapeutic agent under fluid pressure to the treatment site through a delivery interface on the delivery means.

34. The method of claim 33 wherein the support frame is deflected by moving an actuator shaft slidably disposed in a passage through the catheter, the actuator shaft being coupled at its distal end to the support frame.

35. The method of claim 33 wherein the support frame is deflected by moving an actuator shaft slidably disposed in a passage through the catheter, the actuator shaft being coupled at its distal end to cam means for engaging the support frame.

36. The method of claim 33 further comprising:
 discontinuing delivery of the agent;
 retracting the support frame;
 repositioning the catheter;
 radially re-extending the support frame such that the delivery means contacts a second treatment site; and
 delivering an agent through the delivery interface to a second treatment site.

37. The method of claim 33 wherein the step of radially extending is performed before any of the agent has been communicated to the delivery means.

38. The method of claim 33 wherein the step of delivering comprises injecting the agent through a rigid porous matrix.

39. The method of claim 33 wherein the step of delivering comprises injecting the agent through a perforate bladder coupled to the support frame.

40. The method of claim 33 wherein the step of delivering comprises injecting the agent through a manifold of perforate tubes coupled to the support frame.

41. The method of claim 33 wherein the delivery means comprises an open plenum for carrying the agent, the step of delivering comprising maintaining an open side of the plenum against the treatment site to bathe the treatment site in the agent.

42. The method of claim 41 wherein the agent comprises endothelial cells in a culture medium for seeding the treatment site.

43. The method of claim 33 wherein the step of delivering comprises applying a cell graft to the treatment site.

44. The method of claim 33 wherein the vessel is an artery and the treatment site is a region of stenosis.

45. The method of claim 44 wherein the contact surface of the delivery means is maintained against the treatment site while the agent is delivered for a period of at least 10 minutes.

46. The method of claim 45 wherein the support frame is configured to allow blood to flow past the catheter such that body tissue downstream from the treatment site is perfused while the delivery means is maintained against the treatment site.

47. Apparatus for administering an agent to a treatment site in a body lumen, the apparatus comprising:
 a catheter body having a distal end, a proximal end and a passage therebetween;
 a support frame coupled to the catheter body, the support frame being movable between a retracted position adjacent the catheter body and a deployed position radially extended from the catheter body;
 an actuator shaft extending through the passage and having a distal end for engaging the support frame for moving the support frame between the retracted and deployed positions;
 a platform coupled to the support frame, the platform having a contact surface for contacting the treatment site in the deployed position and a delivery interface for delivering the agent to the treatment site, wherein the delivery interface is selected from the group consisting of a rigid porous matrix, a perforate bladder, a manifold of perforate tubes, an open plenum surrounded by a peripheral contact surface, and a support membrane for applying a cell graft.

48. The apparatus of claim 47 wherein the support frame comprises at least a first beam having a first end connected to the catheter body and a second end connected to the platform, the second end being radially deflectable from the catheter body.

49. The apparatus of claim 48 wherein the support frame further comprises a second beam having a third end connected to the actuator shaft and a radially-deflectable fourth end connected to the platform, the distance between the first and third ends being greater than the distance between the second and fourth ends, wherein the third end may be drawn toward the first end by the actuator shaft to radially deflect the second and fourth ends.

50. The apparatus of claim 48 further comprising cam means attached to the distal end of the actuator shaft, the cam means movable against the first beam by means of the actuator shaft to deflect the second end.

51. The apparatus of claim 47 wherein the support frame comprises a first beam having a first end connected to the actuator shaft and a second end connected to the delivery interface, wherein the second end is radially deflectable from the catheter body.

52. The apparatus of claim 51 further comprising cam means fixed to the catheter body near the distal end, the cam means configured to engage the first beam by moving the actuator shaft, thereby deflecting the second end.

53. The apparatus of claim 47 wherein the porous matrix is sintered metal.

54. Apparatus for administering an agent to a treatment site in a body lumen, the apparatus comprising:
a catheter body having a distal end, a proximal end and a passage therebetween;
a support frame coupled to the catheter body, the support frame being movable between a retracted position adjacent the catheter body and a deployed position radially extended from the catheter body;
an actuator shaft extending through the passage and having a distal end for engaging the support frame for moving the support frame between the retracted and deployed positions;
a platform coupled to the support frame, the platform having a contact surface for contacting the treatment site in the deployed position and a delivery interface for delivering the agent to the treatment site; and
a collapsible drug-containing capsule disposed in the distal end of the catheter body and a feeder tube for connecting the capsule to the delivery interface.

55. The apparatus of claim 54 wherein the support frame comprises at least a first beam having a first end connected to the catheter body and a second end connected to the platform, the second end being radially deflectable from the catheter body.

56. The apparatus of claim 55 wherein the support frame further comprises a second beam having a third end connected to the actuator shaft and a radially-deflectable fourth end connected to the platform, the distance between the first and third ends being greater than the distance between the second and fourth ends, wherein the third end may be drawn toward the first end by the actuator shaft to radially deflect the second and fourth ends.

57. The apparatus of claim 55 further comprising cam means attached to the distal end of the actuator shaft, the cam means movable against the first beam by means of the actuator shaft to deflect the second end.

58. The apparatus of claim 54 wherein the support frame comprises a first beam having a first end connected to the actuator shaft and a second end connected to the delivery interface, wherein the second end is radially deflectable from the catheter body.

59. The apparatus of claim 58 further comprising cam means fixed to the catheter body near the distal end, the cam means configured to engage the first beam by moving the actuator shaft, thereby deflecting the second end.

60. The apparatus of claim 54 further comprising a drug supply actuator for collapsing the capsule, the drug supply actuator comprising a piston slidably disposed in the aperture and a rod coupled to the piston and extending through an actuator passage in the catheter body.

61. The apparatus of claim 60 wherein the feeder tube is selectively connectable to the capsule.

62. The apparatus of claim 61 wherein the capsule is slidably disposed in the aperture so as to be movable into engagement with the feeder tube by the piston.

63. The apparatus of claim 62 wherein the feeder tube comprises a sharpened tip for piercing the capsule.

64. A method of administering an agent to a treatment site in a wall of a vessel, the method comprising the steps of:
transluminally positioning a catheter in the vessel with a distal end of the catheter adjacent the treatment site;
radially extending a support frame at the distal end of the catheter such that a contact surface of delivery means coupled to the support frame is against the treatment site;
communicating an agent to the delivery means; and
delivering the agent to the treatment site through a delivery interface on the delivery means, wherein the delivery interface is selected from the group consisting of a rigid porous matrix, a perforate bladder, a manifold of perforate tubes, an open plenum, and a support membrane for applying a cell graft.

65. The method of claim 64 wherein the support frame is deflected by moving an actuator shaft slidably disposed in a passage through the catheter, the actuator shaft being coupled at its distal end to the support frame.

66. The method of claim 64 wherein the support frame is deflected by moving an actuator shaft slidably disposed in a passage through the catheter, the actuator shaft being coupled at its distal end to cam means for engaging the support frame.

67. The method of claim 64 further comprising:
discontinuing delivery of the agent;
retracting the support frame;
repositioning the catheter;
radially re-extending the support frame such that the delivery means contacts a second treatment site; and
delivering an agent through the delivery interface to a second treatment site.

68. The method of claim 64 wherein the step of radially extending is performed before any of the agent has been communicated to the delivery means.

69. The method of claim 64 wherein the agent comprises endothelial cells in a culture medium for seeding the treatment site through an open plenum delivery interface.

70. The method of claim 64 wherein the vessel is an artery and the treatment site is a region of stenosis.

71. A method of administering an agent to a stenosis site in a wall of an artery, the method comprising the steps of:
transluminally positioning a catheter in the vessel with a distal end of the catheter adjacent the treatment site;
radially extending a support frame at the distal end of the catheter such that a contact surface of delivery means coupled to the support frame is against the treatment site;

communicating an agent to the delivery means; and delivering the agent to the treatment site through a delivery interface on the delivery means, wherein the contact surface of the delivery means is maintained against the treatment site while the agent is delivered for a period of at least 10 minutes.

72. The method of claim 71 wherein the support frame is configured to allow blood to flow past the catheter such that body tissue downstream from the treatment site is perfused while the delivery means is maintained against the treatment site.

* * * * *